(12) United States Patent
Maffessanti et al.

(10) Patent No.: US 11,439,357 B2
(45) Date of Patent: Sep. 13, 2022

(54) INTEGRATED ASSESSMENT OF ELECTRICAL ACTIVATION AND MYOCARDIAL STRAIN

(71) Applicant: BIOSENSE WEBSTER (ISRAEL) LTD., Yokneam (IL)

(72) Inventors: Francesco Maffessanti, Sovere BG (IT); Angelo Auricchio, Ruvigliana (CH); Hanspeter Fischer, Schwaz (AT); Frits W. Prinzen, RB Maastricht (NL)

(73) Assignee: BIOSENSE WEBSTER (ISRAEL) LTD., Yokneam (IL)

( * ) Notice: Subject to any disclaimer, the term of this patent is extended or adjusted under 35 U.S.C. 154(b) by 46 days.

(21) Appl. No.: 16/774,325

(22) Filed: Jan. 28, 2020

(65) Prior Publication Data

US 2020/0155082 A1 May 21, 2020

Related U.S. Application Data

(62) Division of application No. 15/614,111, filed on Jun. 5, 2017, now Pat. No. 10,542,941.

(51) Int. Cl.
*A61B 5/00* (2006.01)
*A61B 5/11* (2006.01)
(Continued)

(52) U.S. Cl.
CPC ............ *A61B 5/7282* (2013.01); *A61B 5/062* (2013.01); *A61B 5/1104* (2013.01);
(Continued)

(58) Field of Classification Search
None
See application file for complete search history.

(56) References Cited

U.S. PATENT DOCUMENTS

| 5,738,096 A | 4/1998 | Ben-Haim |
| 6,616,684 B1 * | 9/2003 | Vidlund ............ A61B 17/00234 606/213 |

(Continued)

FOREIGN PATENT DOCUMENTS

| CN | 103957792 A | 7/2014 |
| CN | 106232001 A | 12/2016 |

(Continued)

OTHER PUBLICATIONS

Extended European Search Report for European Application No. 18175714.7, dated Apr. 11, 2019, 8 pages.
(Continued)

*Primary Examiner* — Brian T Gedeon
(74) *Attorney, Agent, or Firm* — Etan S. Chatlynne; Roberts Calderon Safran & Cole P.C.

(57) ABSTRACT

A method for anatomical diagnosis includes measuring, using a catheter that includes a position sensor and an electrode, over multiple cycles of a beating heart, electrical activity and mechanical motion at a plurality of locations contacted by the catheter on a heart wall within a chamber of the heart. Based on the measured mechanical motion, a magnitude of a mechanical strain is computed over the cycles at the locations. In one embodiment, the computed strain is used in identifying a group of the locations at which the magnitude of the mechanical strain is below a predefined strain threshold and a voltage of the electrical activity is below a predefined voltage threshold as a locus of scar tissue. In another embodiment, a pathological condition of the heart is identified based on a characteristic of the mechanical strain computed over the left ventricle during the diastolic phase.

18 Claims, 4 Drawing Sheets

(51) Int. Cl.
    *G16H 50/20*     (2018.01)
    *A61B 5/06*     (2006.01)
    *G16H 40/63*     (2018.01)
    *G16H 20/40*     (2018.01)
    *A61B 5/283*     (2021.01)
    *G16H 20/17*     (2018.01)
    *G16H 40/20*     (2018.01)
    *G16H 30/20*     (2018.01)

(52) U.S. Cl.
    CPC ............ *A61B 5/1107* (2013.01); *A61B 5/283* (2021.01); *A61B 5/6852* (2013.01); *G16H 20/40* (2018.01); *G16H 40/63* (2018.01); *G16H 50/20* (2018.01); *G16H 20/17* (2018.01); *G16H 30/20* (2018.01); *G16H 40/20* (2018.01)

(56) References Cited

U.S. PATENT DOCUMENTS

| | | |
|---|---|---|
| 2002/0087089 A1 | 7/2002 | Ben-Haim |
| 2006/0079736 A1* | 4/2006 | Chin .................... A61M 25/09 600/151 |
| 2008/0021336 A1 | 1/2008 | Dobak, III |
| 2011/0144510 A1 | 6/2011 | Ryu et al. |
| 2011/0152741 A1 | 6/2011 | Banchieri et al. |
| 2011/0172539 A1* | 7/2011 | Ranjbar ................ G09B 23/30 600/453 |
| 2012/0219521 A1* | 8/2012 | Michal .................... A61P 9/00 424/78.37 |
| 2014/0142406 A1 | 5/2014 | Keel et al. |
| 2015/0228254 A1 | 8/2015 | Olson |
| 2015/0289769 A1 | 10/2015 | Venkatesh et al. |
| 2015/0313482 A1 | 11/2015 | Nabutovsky et al. |
| 2015/0313511 A1 | 11/2015 | Nabutovsky et al. |
| 2015/0313550 A1* | 11/2015 | Razavi .................. A61B 5/062 600/508 |
| 2016/0098833 A1* | 4/2016 | Tsadok ................ G06K 9/6201 382/103 |
| 2017/0071675 A1 | 3/2017 | Dawoud et al. |

FOREIGN PATENT DOCUMENTS

| | | |
|---|---|---|
| JP | 2001502189 A | 2/2001 |
| JP | 2001502556 A | 2/2001 |
| JP | 2002505172 A | 2/2002 |
| JP | 2010517644 A | 5/2010 |
| WO | 9724981 A2 | 7/1997 |
| WO | 2015164667 A1 | 10/2015 |
| WO | 2015171393 A1 | 11/2015 |

OTHER PUBLICATIONS

Extended European Search Report for European Application No. 19162964.1, dated Apr. 26, 2019, 9 pages.

* cited by examiner

INTEGRATED ASSESSMENT OF ELECTRICAL ACTIVATION AND MYOCARDIAL STRAIN

CROSS-REFERENCE TO RELATED APPLICATION

The present application is a Divisional application under 35 U.S.C. § 121 of U.S. patent application Ser. No. 15/614, 111, filed Jun. 5, 2017. The entire contents of this application is incorporated by reference herein in its entirety.

FIELD OF THE INVENTION

The present invention relates generally to methods and apparatus for methods and systems for diagnosis and treatment of pathological conditions in the heart, and specifically to integrated electrical and mechanical assessment of the heart using a mapping catheter.

BACKGROUND

Normal functioning of the heart involves substantial deformation of the heart chambers in the cycle of systolic contraction and diastolic expansion. This deformation can be quantified in terms of mechanical strain, which is a deformation descriptor in terms of relative displacement of particles in the body that excludes rigid motion (measuring, for example, the displacement between points in the myocardium relative to reference positions of the points at a selected annotation time in the heart cycle). A number of pathologies in the heart, such as areas of ischemic cardiomyopathy (commonly referred to as "scar tissue") and congestive heart failure, manifest themselves in abnormal (usually abnormally low) levels of strain or as abnormal timing distribution of strain. Such pathologies are most commonly evaluated by diagnostic imaging, using cardiac magnetic resonance imaging (MRI) or ultrasound, for example.

Mechanical functioning of the heart can also be measured invasively, using a mapping catheter that is inserted into the heart. For example, U.S. Pat. No. 5,738,096, whose disclosure is incorporated herein by reference, describes a method of constructing a cardiac map that includes bringing an invasive probe into contact with a location on a wall of the heart, determining, at two or more phases of the heart cycle, a position of the invasive probe, and determining a local non-electrical physiological value at the location. The method is repeated for a plurality of locations in the heart. The positions are combined to form a time-dependent map of at least a portion of the heart, and local relationships between changes in positions of the invasive probe and determined local non-electrical physiological values are determined. Preferably, local electrical activity at the plurality of locations is also acquired. The NOGA® system offered by Biosense Webster Inc. (Diamond Bar, Calif.) is configured for performing these sorts of measurements.

As another example, U.S. Patent Application Publication 2015/0228254 describes a method of generating an anatomical map, which includes acquiring geometry information and biological information for an anatomical region. The geometry and biological information are associated with each other, for example by associating measured biological attributes with the anatomical locations at which they were measured. A graphical representation of the anatomical region, including a map of at least two biological attributes, can then be superimposed upon a geometric model of the anatomical region.

SUMMARY

Embodiments of the present invention that are described hereinbelow provide improved methods and systems for cardiologic diagnosis.

There is therefore provided, in accordance with an embodiment of the invention, a method for anatomical diagnosis, which includes measuring, using a catheter including a position sensor and an electrode, over multiple cycles of a beating heart, electrical activity and mechanical motion at a plurality of locations contacted by the catheter on a heart wall within a chamber of the heart. Based on the measured mechanical motion, a magnitude of a mechanical strain is computed over the cycles at the locations. A group of the locations at which the magnitude of the mechanical strain is below a predefined strain threshold and a voltage of the electrical activity is below a predefined voltage threshold is identified as a locus of scar tissue, while identifying as potentially viable one or more loci at which the mechanical strain is above the predefined strain threshold or the voltage is above the predefined voltage threshold.

In a disclosed embodiment, measuring the electrical activity includes measuring a unipolar voltage.

In some embodiments, measuring the mechanical motion includes measuring, using the position sensor, trajectories of the locations while a distal end of the catheter is held in contact with the heart wall at each of the locations, and computing the magnitude of the mechanical strain includes calculating, based on the trajectories, changes in distance between neighboring locations over the cycles of the heart. In a disclosed embodiment, calculating the changes in distance includes finding differences in the distance between first coordinates measured during a diastolic phase of the heart and second coordinates measured during a systolic phase of the heart. Additionally or alternatively, computing the magnitude of the mechanical strain includes computing, based on the changes in the distance, a measure of the mechanical strain selected from a group of measures consisting of a circumferential strain, a longitudinal strain, and an area strain.

In some embodiments, the method includes placing one or more pacing electrodes in the chamber of the heart at one or more of the potentially viable loci or injecting a therapeutic substance into the heart wall in the chamber of the heart at one or more of the potentially viable loci.

There is also provided, in accordance with an embodiment of the invention, a method for anatomical diagnosis, which includes measuring, using a catheter including a position sensor, over multiple cycles of a beating heart, mechanical motion at a plurality of locations contacted by the catheter on a heart wall within a left ventricle of the heart. Based on the measured mechanical motion, a mechanical strain is computed at a diastolic phase of the cycles at the locations. A pathological condition of the heart is identified based on a characteristic of the mechanical strain computed over the left ventricle during the diastolic phase.

In one embodiment, identifying the pathological condition includes detecting a time of maximal volume of the left ventricle during the diastolic phase, and finding, based on the computed mechanical strain, a difference between a time of maximal local strain and the time of maximal global volume of the left ventricle.

Additionally or alternatively, identifying the pathological condition includes calculating, based on the computed mechanical strain, a fraction of the diastolic phase during which the left ventricle is relaxing.

In some embodiments, the catheter includes an electrode, and the method includes measuring electrical activity together with the mechanical motion at the plurality of locations, using the catheter, wherein the pathological condition is identified based on the measured electrical activity together with the mechanical strain. In a disclosed embodiment, measuring the electrical activity includes detecting a time of activation of the heart wall in the left ventricle, and identifying the pathological condition includes comparing locally, based on the computed mechanical strain, a maximal relaxation of the left ventricle and the mechanical strain at the time of activation.

There is additionally provided, in accordance with an embodiment of the invention, a method for anatomical diagnosis, which includes measuring, using a catheter including a position sensor, over multiple cycles of a beating heart, mechanical motion at a plurality of locations contacted by the catheter on a heart wall within a left ventricle of the heart. Based on the measured mechanical motion, a mechanical strain is computed at a diastolic phase of the cycles at the locations. A group of the locations is identified at which a peak timing of the mechanical strain is not synchronous.

In a disclosed embodiment, the method includes measuring an intracardiac pressure in the left ventricle, and applying the measured intracardiac pressure, together with the mechanical strain, in diagnosing a pathological condition of the heart.

There is further provided, in accordance with an embodiment of the invention, a system for anatomical diagnosis, including a catheter having a distal end configured for insertion into a chamber of a beating heart and including a position sensor and an electrode. A processor is configured to measure, responsively to signals received from the electrode and the position sensor over multiple cycles of the beating heart, electrical activity and mechanical motion at a plurality of locations contacted by the catheter on a heart wall within the chamber of the heart, and to compute, based on the measured mechanical motion, a magnitude of a mechanical strain over the cycles at the locations, and to identify a group of the locations at which the magnitude of the mechanical strain is below a predefined strain threshold and a voltage of the electrical activity is below a predefined voltage threshold as a locus of scar tissue, while identifying as potentially viable one or more loci at which the mechanical strain is above the predefined strain threshold or the voltage is above the predefined voltage threshold.

There is moreover provided, in accordance with an embodiment of the invention, a system for anatomical diagnosis, including a catheter having a distal end configured for insertion into a chamber of a beating heart and including a position sensor. A processor is configured to measure, responsively to signals received from the position sensor over multiple cycles of the beating heart, mechanical motion at a plurality of locations contacted by the catheter on a heart wall within a left ventricle of the heart, and to compute, based on the measured mechanical motion, a mechanical strain at a diastolic phase of the cycles at the locations, and to identify a pathological condition of the heart based on a characteristic of the mechanical strain computed over the left ventricle during the diastolic phase.

There is furthermore provided, in accordance with an embodiment of the invention, a computer software product, including a non-transitory computer-readable medium in which program instructions are stored, which instructions, when read by a computer, cause the computer to receive signals output by a catheter having a distal end inserted into a chamber of a beating heart and including a position sensor and an electrode, and to measure, responsively to the signals received from the electrode and the position sensor over multiple cycles of the beating heart, electrical activity and mechanical motion at a plurality of locations contacted by the catheter on a heart wall within the chamber of the heart, and to compute, based on the measured mechanical motion, a magnitude of a mechanical strain over the cycles at the locations, and to identify a group of the locations at which the magnitude of the mechanical strain is below a predefined strain threshold and a voltage of the electrical activity is below a predefined voltage threshold as a locus of scar tissue, while identifying as potentially viable one or more loci at which the mechanical strain is above the predefined strain threshold or the voltage is above the predefined voltage threshold.

There is also provided, in accordance with an embodiment of the invention, a computer software product, including a non-transitory computer-readable medium in which program instructions are stored, which instructions, when read by a computer, cause the computer to receive signals output by a catheter having a distal end inserted into a chamber of a beating heart and including a position sensor, and to measure, responsively to signals received from the position sensor over multiple cycles of the beating heart, mechanical motion at a plurality of locations contacted by the catheter on a heart wall within a left ventricle of the heart, and to compute, based on the measured mechanical motion, a mechanical strain at a diastolic phase of the cycles at the locations, and to identify a pathological condition of the heart based on a characteristic of the mechanical strain computed over the left ventricle during the diastolic phase.

The present invention will be more fully understood from the following detailed description of the embodiments thereof, taken together with the drawings in which:

DETAILED DESCRIPTION OF EMBODIMENTS

Figure 1:
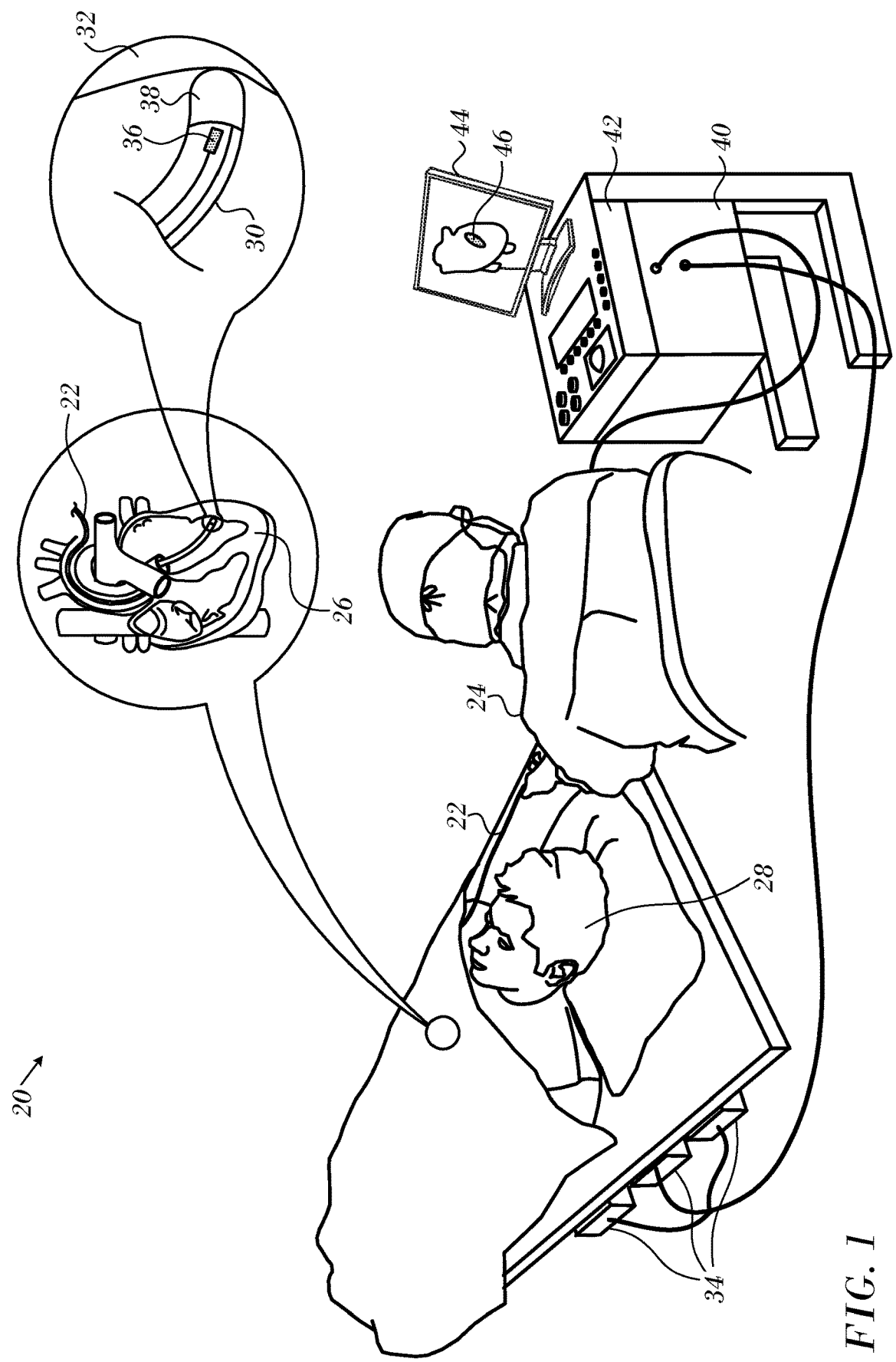
FIG. 1 is a schematic pictorial illustration of a system for electro-anatomical and electromechanical diagnosis of the heart, in accordance with an embodiment of the invention.

Cardiac MRI, by means of tagging sequences, is widely regarded as the "gold standard" for evaluating mechanical functioning of the heart. For example, heart wall displacement measured in successive tagged MR images over the heart cycle can be used to compute local strain of the myocardium. Areas of systolic low strain are secondary to myocardial reduced function, as a consequence of locally reduced contractility, and are likely to be associated with the presence of scar tissue. Conversely, abnormal strain patterns during diastole may be secondary to impaired myocardial relaxation, hampering the physiological diastolic perfusion of the viable myocardium. As another example, the dispersion of the local peak of systolic strain can be indicative of dyssynchronous contraction, which has been associated with electrical conduction disturbance.

Cardiac MRI, however, suffers from limited temporal resolution and is able to measure strains reliably only during the systolic phase (due to fading of the hypermagnetized grid that is used to derive the strain measurements). Perhaps, at least in part, for this reason, studies of myocardial strain and other aspects of the mechanical functionality of the heart have focused on the systolic phase, and the diagnostic value of diastolic strain measurements has been overlooked.

Embodiments of the present invention that are described herein provide improved methods and systems for invasive measurement of myocardial strain, which overcome some of the shortcomings of MRI and other existing modalities. These embodiments are built around a system such as the above-mentioned NOGA system (or the CARTO® system, also offered by Biosense Webster Inc.) and use a catheter comprising a position sensor and an electrode and/or a pressure sensor for measuring intracardiac pressure. Alternatively or additionally, the catheter comprises a sensor for evaluating contact force against the cardiac wall.

The distal end of the catheter is inserted into a chamber of a beating heart, such as the right or left ventricle, or other parts of the heart, such as the atria or coronary sinus. Based on signals received from the position sensor over multiple cycles of the beating heart, a processor measures changes in position, and thus mechanical motion, at locations contacted by the catheter on the heart wall within the chamber and computes, based on the measured mechanical motion, the mechanical strain within the heart wall at different phases of the heart cycle. In some embodiments, as noted below, the processor receives and processes electrical signals from the electrode(s) on the catheter together with the position signals.

Based on variations in the strain over the heart cycle, and possibly the interplay of local mechanical and electrical activation of the myocardial tissue, the processor is able to identify the locations of suspected pathologies in the heart. These diagnostic results can be used in guiding therapeutic intervention, for example, in selecting viable locations at which to place pacing electrodes or inject biologically active substances, such as cells or drugs, in the chamber of the heart. The enhanced myocardial tissue characterization and diagnostic accuracy of the present techniques makes it possible to optimize the locations at which therapy is applied and thus improve the clinical efficacy of cardiac resynchronization treatment and other therapies for ameliorating congestive heart failure, as well as other disease conditions of the heart.

In some embodiments, the catheter is used to measure electrical activity, as well as mechanical motion, at the locations contacted by the catheter on the heart wall. Although catheter-based measurement of electrical activity has been analyzed by itself in many studies and is widely used in diagnostic procedures, and mechanical analysis of cardiac images is also common, the combination of these two separate modalities is little known in clinical practice. In the present embodiments, on the other hand, mechanical and electrical properties are measured simultaneously by the catheter in a single pass and are thus registered with one another inherently, with essentially perfect precision.

On this basis, a group of the locations at which both the magnitude of the mechanical strain is below a predefined strain threshold and the voltage of the electrical activity is below a predefined voltage threshold can be identified as a locus of scar tissue. The inventors have found that this combined application of mechanical and electrical criteria achieves more accurate diagnosis and delineation of scar tissue than either mechanical or electrical measurements alone. By the same token, areas in which the mechanical strain is above the predefined strain threshold or the voltage is above the predefined voltage threshold can be identified as loci of potentially viable tissue. This identification is useful in targeting therapeutic means, such as pacing electrodes or injections of therapeutic substances, at locations where they are likely to be most effective.

In other embodiments, the processor computes, based on the measured mechanical motion, the mechanical strain in the heart wall during the diastolic phase and uses these diastolic measurements in identifying pathological conditions of the heart. These diastolic measurements can be particularly useful in diagnosing defects in the relaxation of the heart muscle, which can be the cause of both low pumping efficiency and poor perfusion of the myocardium.

FIG. 1 is a schematic pictorial illustration of a system 20 for electro-anatomical and electromechanical diagnosis, in accordance with an embodiment of the invention. An operator 24 (typically a cardiologist) inserts a catheter 22 through the vascular system of a patient 28 into the patient's heart 26. In the pictured embodiment, a distal end 30 of the catheter has been inserted through the aorta into the left ventricle; but the techniques described herein may alternatively be applied using other approach paths, as well as in any chamber of the heart.

In the present embodiment, distal end 30 of catheter 22 comprises a position sensor 36 and at least one electrode 38. Position sensor 36 in the present example comprises one or more miniature sensing coils, which sense magnetic fields generated by one or more field generator coils 34 outside the patient's body. This sort of magnetic position sensing scheme is used in the above-mentioned NOGA system. Alternatively, system 20 may implement any other suitable sort of position sensing that is known in the art, such as electrical or ultrasonic position sensing. Optionally, distal end 30 may comprise other sorts of sensing elements that are known in the art, such as a pressure sensor for sensing the force exerted by the distal tip of the catheter against a heart wall 32, or sensors of intracardiac pressure for hemodynamic evaluation.

Operator 24 brings distal end 30 into contact with multiple locations on heart wall 32 of the chamber whose function is to be diagnosed. At each location, a control unit 40 receives and processes the signals output by position sensor 36 in order to compute three-dimensional (3D) location coordinates of the distal tip of catheter 22, and thus of the contacted location on heart wall 32. Control unit 40 also receives electrical signals from electrode 38, which are indicative of local voltages in the heart wall. Typically, operator 24 holds distal end 30 in contact with each location over one or more heart cycles, thus enabling control unit 40 to collect data with respect to both the variation in the electrical signals and the motion of the 3D location coordinates over multiple cycles of beating heart 26.

Based on the data provided by control unit 40, a processor 42 measures both electrical activity and mechanical motion at each of the locations contacted by catheter 22 on heart wall 32. Processor 42 assembles these data into a dynamic 3D map of the heart chamber of interest, showing both the changes in mechanical shape and the electrical activity over the inner surface of the chamber over the course of a heart cycle, including both systolic and diastolic phases. Based on the measured mechanical motion, processor 42 computes the mechanical strain at different locations in the chamber. Processor 42 may display the 3D map graphically, for example on a display 44. The map is annotated to indicate parameters and features of diagnostic interest, such as a scar 46, or areas of impaired or non-synchronous contraction or relaxation, or of inappropriate electrical and mechanical impulse propagation or altered electromechanical coupling. Techniques for computation of the strain and extraction of parameters and features based on the strain are described in detail hereinbelow.

System 20 may be built around catheters and control units that are known in the art, such as the NOGA system described above. Processor 42 typically comprises a general-purpose computer processor, which has suitable interfaces for receiving data inputs and outputting diagnostic information, and which is programmed in software to carry out the functions that are described herein. The software may be downloaded to system 20 in electronic form, over a network, for example. Additionally or alternatively, the software may be stored on tangible, non-transitory computer-readable media, such as optical, magnetic or electronic memory media.

Figure 2A:
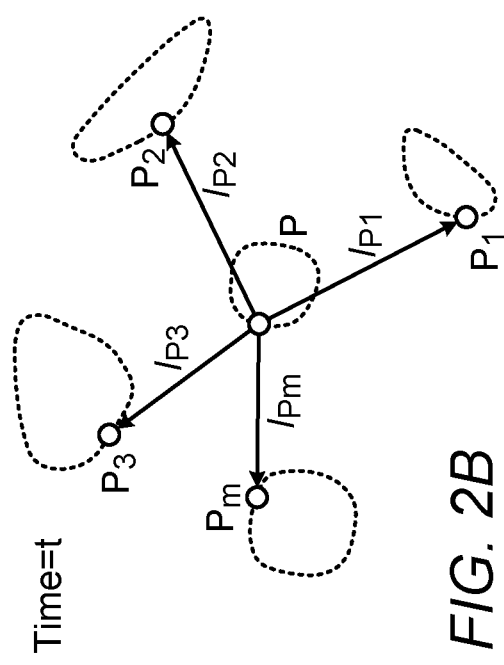
FIGS. 2A and 2B are graphs that schematically illustrate changes in displacement measured between locations in the myocardium at different times during a heart cycle, in accordance with an embodiment of the invention.
Figure 2B:
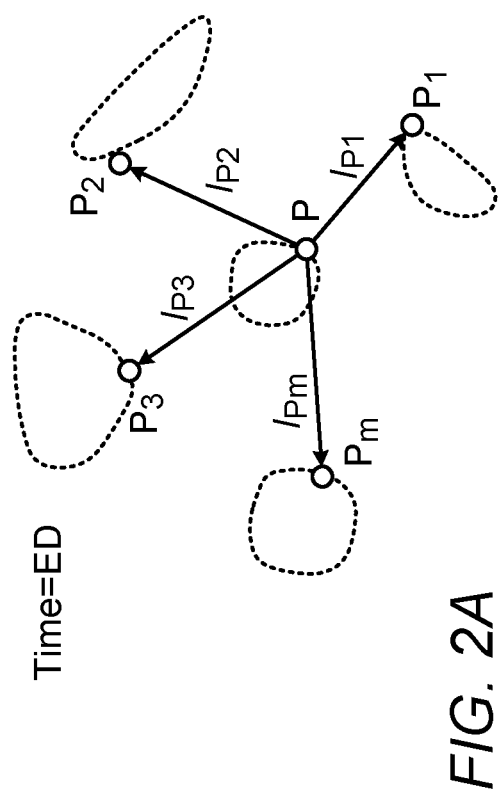

FIGS. 2A and 2B are graphs that schematically illustrate changes in displacement measured by catheter 22 between locations in the myocardium at different times during a heart cycle, in accordance with an embodiment of the invention. These changes are found by measuring, using position sensor 36, trajectories of locations on heart wall 32 while distal end 30 of catheter 22 is held in contact with the heart wall at each of the locations, and calculating, based on the trajectories, changes in the distances between neighboring locations over one or more cycles of the heart. Specifically, this technique is used to find the differences in the distances between coordinates measured at peak relaxation and/or end-diastole of the heart and the distances at other times in the heart cycle, including at the peak of contraction of the heart in systole. End-diastole is defined as the time during the heart cycle at which the left ventricle reaches its maximal volume, as measured, for example, by integrating the volume contained within the dynamic 3D map of the left ventricle computed by processor 42.

The displacement in the pictured example is measured in terms of local linear shortening (LLS) of the distances $l_1, l_2, \ldots, l_m$ between a point P (corresponding to a location on the heart wall contacted by catheter 22) and neighboring location points $P_1, P_2, \ldots, P_m$. The distances are determined from the catheter coordinates in the dynamic 3D map produced by system 20. The change in LLS is measured between a reference time at end-diastole (ED), shown in FIG. 2A, and a time t during the heart cycle shown in FIG. 2B.

For each point P, processor 42 computes the strain in terms of a weighted sum of the distances from the neighboring points:

$$l_p = \sum_m w_{P_m}^{ED} \cdot l_{P_m}$$

The weights $w_{P_m}^{ED}$ are a function of distance between the current point p and the general point m, evaluated at the annotation time (end-diastole). The weight function can be a cubic or Gaussian function, for example. The distance between points to be used in computing the weights is measured on the surface of the heart, to avoid the effect of close points belonging to opposite cardiac walls. Points that are too far (i.e., whose distance from P is greater than $D_{max}$) or too close (i.e., whose distance is shorter than $D_{min}$) are not weighted in the computation of strain. $D_{min}$ and $D_{max}$ are user-defined parameters.

A Gaussian weight function to be used in the above formula can be computed as follows:

$$W_{P_m}^{ED} = e^{-\frac{(l_{P_m}(ED) - D_{mean})^2}{\sigma^2}} \quad \text{for } D_{min} < l_{P_m} D_{max}$$

$$W_{P_m}^{ED} = 0 \quad \text{otherwise}$$

Assuming $$D_{mean} = \frac{D_{max}}{2}$$

(or some user-defined value) and $$\sigma = \frac{D_{max} - D_{min}}{3}$$

we obtain the normalized weights:

$$W_{P_m}^{ED} = \frac{W_{P_m}^{ED}}{\sum_m W_{P_m}^{ED}}$$

The strain at point P at time t is then given by:

$$LLS_P(t) = \frac{l_p(t) - l_p(ED)}{l_p(ED)}$$

The strain measured in this manner will thus be negative through most or all of the heart cycle. The magnitude of the strain (i.e., the absolute value of LLS) will typically reach its maximum at the peak of local contraction, in correspondence to the ventricular systole in a synchronous heart.

The inventors have evaluated a number of measures of the strain of the heart wall that can be used for purposes of diagnostic evaluation, such as longitudinal strain, i.e., deformation along the apex-to-mitral plane direction, and the circumferential strain, perpendicular to the longitudinal direction. The two directional strain components can been obtained by computing and then diagonalizing the Cauchy-Green deformation gradient tensor with respect to the reference time (end-diastole). Local area strain (LAS), defined as the square root of the product of the longitudinal strain by the circumferential strain, was found to give the best results, in terms of diagnostic sensitivity and specificity, in identifying pathological features such as scars in the myocardium.

Figure 3:
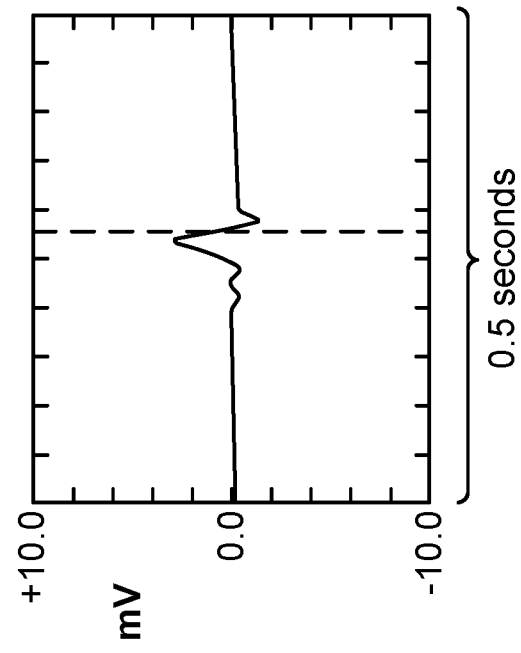
FIG. 3 is a plot that schematically illustrates an electrical activation wave measured at a location in the heart, in accordance with an embodiment of the invention.

FIG. 3 is a plot that schematically illustrates an electrical activation wave measured by electrode 38 at the distal tip of catheter 22 at a location in heart 26, in accordance with an embodiment of the invention. Electrode 38 generates a unipolar electrogram at each location contacted by distal end 30 of catheter 22. (Alternatively or additionally, bipolar electrograms may be used.) The vertical line in FIG. 3 shows the time of activation at the location in question. The amplitude of the electrogram gives an indication of the strength of the electrical activity in the myocardial tissue at the location. As noted earlier, healthy tissue is characterized by both a high magnitude of strain and strong electrogram signals, in comparison with lower values measured in scar tissue, while tissue that is still viable but ischemic may exhibit diminished values of one or both of these measures of tissue health.

Figure 4:
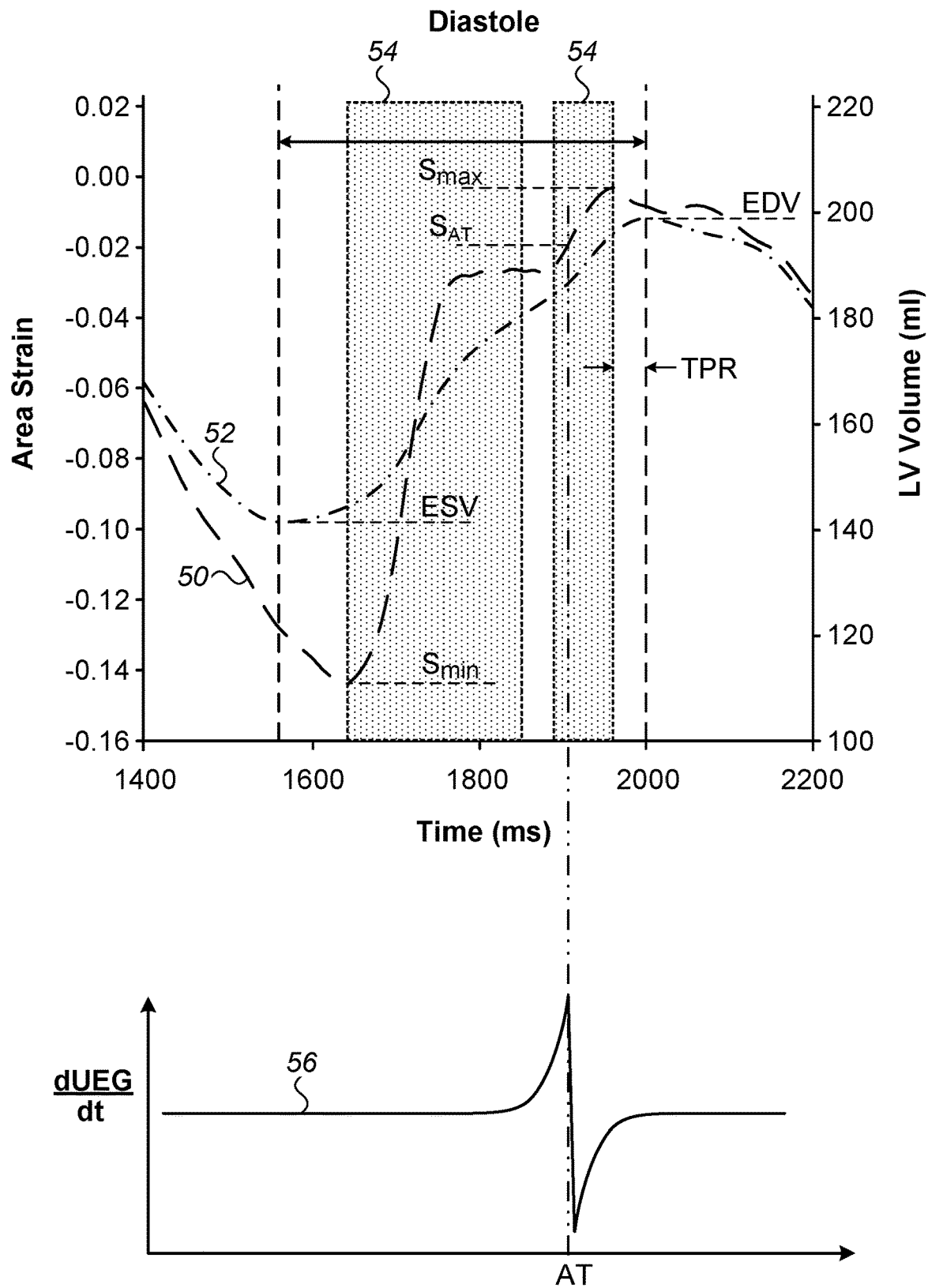
FIG. 4 is a plot that schematically illustrates measurements of left ventricular volume, strain, and electrical activation over the course of a heart cycle, in accordance with an embodiment of the invention.

FIG. 4 is a plot that schematically illustrates measurements of left ventricular volume, strain, and electrical activation measured by system 20 over the course of a heart cycle, in accordance with an embodiment of the invention. A strain curve 50 shows the computed area strain, as defined above, at a given location in the left ventricle. This strain varies from a minimal value $S_{min}$ (at which the magnitude, or absolute value, of the strain is maximal) to a maximum value $S_{max}$ at which the ventricle reaches its most relaxed shape. A volume curve shows the variation in the left-ventricular volume from its minimal end-systolic value (ESV) to its maximal end-diastolic value (EDV). Diastole is marked in FIG. 4 as the period during which the ventricular volume is increasing, i.e., the time from ESV to EDV. Block 54 in FIG. 4 show the portions of diastole during which the slope of strain curve 50 is positive, indicating that the magnitude of the strain is decreasing and thus the heart muscle is relaxing during these periods. An activation derivative curve 56 shows the change in the unipolar electrogram (UEG) voltage over the heart cycle, which is used in deriving the activation time AT.

In a healthy heart, operating with optimal efficiency, the times of EDV, AT, and $S_{max}$ are expected to be well synchronized (as are ESV and $S_{min}$). In other words, the heart is expected to be most relaxed at the time of maximum ventricular volume, at which point electrical activation initiates the next systolic contraction. Good synchronization is also important in maximizing the diastolic filling of the heart chamber and the coronary perfusion of the myocardium, which occurs during diastole. Some pathological conditions of the heart, such as congestive heart failure (CHF) and left bundle branch block (LBBB), on the other hand, can be marked by loss of synchronization between EDV, AT and strain. As noted earlier, however, existing methods of diagnosis, such as cardiac MRI, lose precision during the diastolic phase and thus may be unable to diagnose diastolic defects of this sort.

The inventors have developed a number of quantitative measures that can be used in evaluating the nature and severity of defects in diastolic function based on the values of volume, strain and electrical activation noted above. These measures, which are marked in FIG. 4, include:

1. Time of peak relaxation (TPR), which compares the strain measured at the time of maximal volume of the left ventricle during the diastolic phase (EDV) to the strain at the time of maximal relaxation of the left ventricle ($S_{max}$). Specifically, TPR finds the difference between the time of maximal local strain ($S_{max}$) and the time of maximal global volume of the left ventricle (EDV). When TPR is negative, as shown in FIG. 4, the myocardium reaches its peak of relaxation before the left ventricle has reached what should be the global relaxation point. Large values of TPR are indicative of inefficient pumping and altered myocardial properties (particularly related to tissue elasticity and stiffness).

2. Effective perfusion time (EPT), which indicates the fraction of the diastolic phase during which the left ventricle is relaxing and being perfused. In FIG. 4, this fraction is illustrated by the cumulative duration of blocks 54 relative to the total duration of the diastolic phase. Regional differences and low values of EPT can be indicative of problems in local perfusion of the myocardium, which occurs mainly during the diastolic phase.

3. Relaxation at the time of activation (RAT), which compares, based on the computed mechanical strain, the local relaxation of the left ventricle ($S_{max}$) and the mechanical strain at the time of local electrical activation, $S_{AT}$. RAT may be defined as follows, for example:

$$RAT(\%) = \beta \cdot 100 \cdot \frac{S_{AT} - S_{min}}{S_{max} - S_{min}}$$

The parameter β has the value −1 when $S_{max}$ occurs before AT (as in the example shown in FIG. 4) and +1 otherwise. Negative RAT indicates that depolarization of the heart muscle is beginning before relaxation has peaked.

Low values of EPT can be used, for example, as an indication of the need for local pacing in the left ventricle to ensure adequate perfusion, as well as of areas with "functional" (as opposed to "structural") ischemia. Specifically, research suggests that local ischemias in the heart can result from shortening of the period of diastolic flow in these areas, possibly due to poorly-synchronized local strain. Variations in EPT values can help to identify the areas in the heart that are at risk of being functionally under-perfused due to abnormal wall motion in the diastolic phase. Once these areas are identified, the local conditions can be treated by appropriate application of pacing electrodes and/or other therapies to correct the synchronization of wall motion.

As another example, efficacy of myocardial fiber contraction is dependent on the level of stretch at the time of electrical activation. Maximally effective contraction force requires that each region of the left ventricle be electrically activated at the time of optimal pre-stretch, meaning the time at which the strain has its maximal value $S_{max}$, meaning that RAT is close to zero. Larger values of RAT, and particularly negative values, are indicative of suboptimal heart wall motion efficacy. Local pacing and other therapies can be applied in order to reduce local RAT and thus enhance cardiac efficiency.

Figure 5:
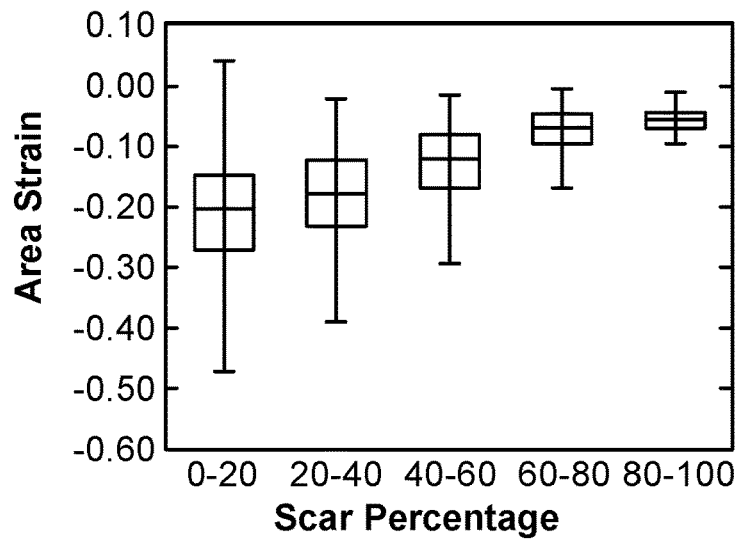
FIG. 5 is a plot that schematically shows a dependence of area strain on scar percentage in the heart, measured in accordance with an embodiment of the invention.

FIG. 5 is a plot that schematically shows a dependence of strain on scar percentage in the heart, measured in accordance with an embodiment of the invention. The strain in this example is represented by area strain, as defined above and measured using system 20. The "scar percentage" refers to the extent of scar tissue within the area under test. It can be seen clearly in the figure that the magnitude of the strain decreased significantly with increasing scar extent, although the measured strain cannot differentiate unequivocally between scarred and viable areas of the tissue. The inventors found in particular that strain values alone lack specificity in identifying areas of non-transmural scar tissue.

Figure 6A:
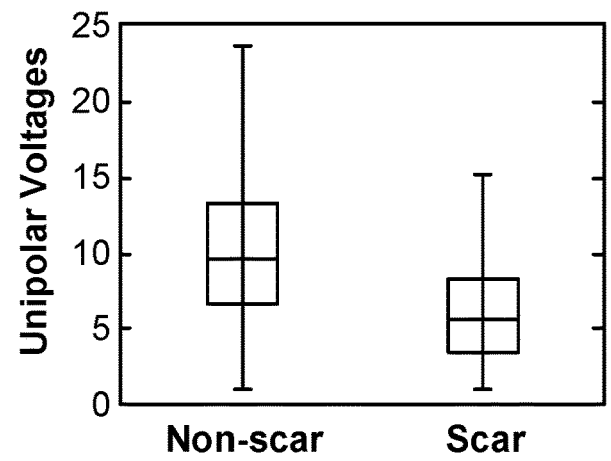
FIGS. 6A and 6B are plots that respectively show differences between unipolar voltages and area strain measured over healthy and scar tissue in the heart, in accordance with an embodiment of the invention.
Figure 6B:
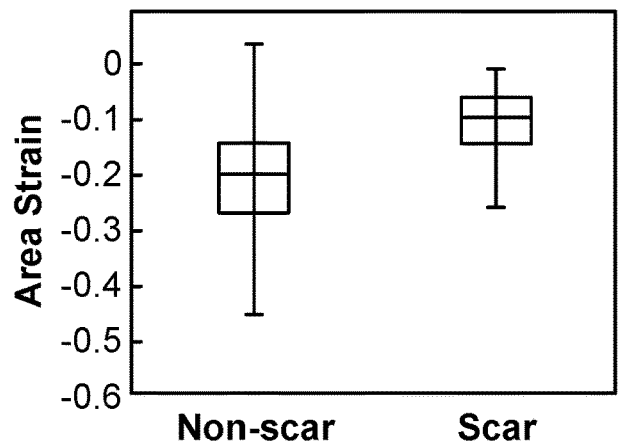

FIGS. 6A and 6B are plots that respectively show differences between unipolar voltages and area strain, respectively, measured by system 20 over healthy and scar tissue in heart 26, in accordance with an embodiment of the invention. The inventors found that when the magnitude of the area strain at a given location was below a certain strain threshold and the voltage of the electrical activity was also below a predefined voltage threshold, the location could be identified as scar tissue with an accuracy of 83%—significantly greater than the accuracy provided by strain or electrical measurements alone.

Although certain measurement techniques and diagnostic parameters are described above as examples of the usefulness of system 20 in diagnosing certain pathologies, other sorts of measures and parameters will be apparent to those skilled in the art after reading the above description and are considered to be within the scope of the present invention. It will thus be appreciated that the embodiments described above are cited by way of illustration, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

The invention claimed is:

1. A method for treating a pathological condition in a heart, comprising:
    measuring, using a catheter comprising a position sensor and an electrode, over multiple cycles of a beating heart, mechanical motion and electrical signals at a plurality of locations on a heart wall within a left ventricle of the heart;
    based on the mechanical motion, computing a mechanical strain of a diastolic phase of at least one of the cycles;
    based on the electrical signals, determining an electrical activity of the heart;
    identifying a pathological condition of the heart based on the electrical activity and the mechanical strain;
    identifying loci of viable tissue based on the electrical activity and the mechanical strain; and
    placing at least one pacing electrode or injecting a therapeutic substance in the loci of viable tissue.

2. The method according to claim 1, wherein the step of measuring the mechanical motion comprises measuring trajectories of the plurality of locations while a distal end of the catheter is held in contact with the heart wall at each of the plurality of locations, and
    wherein the step of computing the mechanical strain comprises calculating, based on the trajectories, changes in distance between neighboring locations of the plurality of locations over the cycles of the heart.

3. The method according to claim 2, wherein the step of calculating the changes in distance comprises determining a first distance between coordinates of the plurality of locations measured during a diastolic phase of the heart and a second distance between the coordinates measured during a systolic phase of the heart, and calculating a difference between the first distance and the second distance.

4. The method according to claim 2, wherein the mechanical strain comprises a circumferential strain, a longitudinal strain, or an area strain.

5. The method according to claim 1, wherein the step of identifying the pathological condition comprises finding, based on the mechanical strain, a difference between a time of maximal local strain and a time of maximal global volume of the left ventricle.

6. The method according to claim 1, wherein the step of identifying the pathological condition comprises calculating, based on the mechanical strain, a fraction of the diastolic phase during which the left ventricle is relaxing.

7. The method according to claim 1, further comprising determining a time of activation of the heart wall in the left ventricle from the electrical activity, and
    wherein the step of identifying the pathological condition comprises comparing a maximal relaxation of the left ventricle and the mechanical strain at the time of activation.

8. A method for anatomical diagnosis, comprising:
    measuring, using a catheter comprising a position sensor, over multiple cycles of a beating heart, mechanical motion at a plurality of locations contacted by the catheter on a heart wall within a left ventricle of the heart;
    based on the measured mechanical motion, computing a mechanical strain at a diastolic phase of the cycles at the locations; and
    identifying a group of the locations at which a peak timing of the mechanical strain is not synchronous.

9. The method according to claim 8, and comprising measuring an intracardiac pressure in the left ventricle, and applying the measured intracardiac pressure, together with the mechanical strain, in diagnosing a pathological condition of the heart.

10. A system for treating a pathological condition in a heart, comprising:
    a catheter having a distal end configured for insertion into a chamber of a beating heart, the catheter comprising a position sensor and an electrode;
    a display; and
    a processor, which is configured to:
        receive position signals from the position sensor over multiple cycles of the beating heart, from a plurality of locations contacted by the catheter on a heart wall within a left ventricle of the heart,
        receive electrical signals from the electrode over multiple cycles of the beating heart, from the plurality of locations,
        compute, based on the position signals, a mechanical strain at a diastolic phase of the multiple cycles,
        determine, based on the electrical signals, an electrical activity of the heart,
        identify, based on the mechanical strain and the electrical activity, a feature of diagnostic interest; and
        display the feature of diagnostic interest on the display.

11. The system according to claim 10, wherein the processor is further configured to compute, using the position signals, trajectories of the plurality of locations while the catheter is held in contact with the heart wall at each of the plurality of locations, and to compute the mechanical strain by calculating, based on the trajectories, changes in distance between neighboring locations of the plurality of locations over the cycles of the heart.

12. The system according to claim 11, wherein the processor is further configured to compute a first distance between coordinates of the plurality of locations measured during a diastolic phase of the heart and a second distance between the coordinates measured during a systolic phase of the heart, and a difference between the first distance and the second distance.

13. The system according to claim 11, wherein the mechanical strain comprises a circumferential strain, a longitudinal strain, or an area strain.

14. The system according to claim 10, wherein the processor is further configured to find, based on the mechanical strain, a difference between a time of a maximal local strain and a time of a maximal global volume of the left ventricle.

15. The system according to claim 10, wherein the processor is further configured to calculate, based on the mechanical strain, a fraction of the diastolic phase during which the left ventricle is relaxing.

16. The system according to claim 10, wherein the processor is further configured to determine, based on the electrical activity, a time of activation of the heart wall in the left ventricle.

17. The system according to claim 10, wherein the feature of diagnostic interest includes a scar.

18. A computer software product, comprising a non-transitory computer-readable medium in which program instructions are stored, which instructions, when read by a computer, cause the computer to receive signals output by a catheter having a distal end inserted into a chamber of a beating heart and including a position sensor and an electrode, and to determine, responsively to position signals received from the position sensor and electrical signals received from the electrode over multiple cycles of the beating heart, mechanical motion at a plurality of locations contacted by the catheter on a heart wall within a left ventricle of the heart and electrical activity of the heart, and to compute, based on the mechanical motion, a mechanical strain at a diastolic phase of the cycles at the locations, and to identify a pathological condition of the heart based on the electrical activity and the mechanical strain.

\* \* \* \* \*